United States Patent [19]

Aloni

[11] Patent Number: 4,507,144
[45] Date of Patent: Mar. 26, 1985

[54] PLANT GROWTH METHOD AND COMPOSITION

[75] Inventor: Roni Aloni, Tel Aviv, Israel

[73] Assignee: Ramot University Authority For Applied Research And Industrial Development, Ltd., Ramat-Aviv, Israel

[21] Appl. No.: 475,212

[22] Filed: Mar. 14, 1983

[30] Foreign Application Priority Data

Apr. 1, 1982 [IL] Israel ............................... 65402

[51] Int. Cl.$^3$ .................. A01N 43/08; A01N 37/38
[52] U.S. Cl. ........................................ 71/89; 71/96; 71/114; 71/115; 71/117
[58] Field of Search ............................. 71/89, 114

[56] References Cited

U.S. PATENT DOCUMENTS 4,110,102  8/1978  Pharis ................................ 71/89

FOREIGN PATENT DOCUMENTS 513651  2/1976  Japan ............................... 71/89
1590625  6/1981  United Kingdom ............ 71/89

OTHER PUBLICATIONS

Hasman et al., "Investigations on Auxin, etc.", (1961), CA 56, pp. 6406-6407, (1962).
Chardenon et al., "The Effects of Gibberellic, etc.", (1963), CA 60, p. 13807d., (1964).
Spanjersberg et al., "Action of Gibberellic etc.", (1964), CA 61, p. 3627f., (1964).
Yates, "Coadministration of Gibberellin etc.", (1973), CA 84, No. 85457m., (1976).

Primary Examiner—Glennon H. Hollrah
Attorney, Agent, or Firm—Browdy and Neimark

[57] ABSTRACT

There is provided a process of increasing the fiber crop of plants cultivated for their content, which comprises applying to same in combination, an auxin and a gibberellin a number of times, and harvesting the crop after the plants reach the desired stage of growth, and a composition for increasing the fiber content of cultivated plants comprising in combination a gibberellin and an auxin.

4 Claims, No Drawings

4,507,144

PLANT GROWTH METHOD AND COMPOSITION

FIELD OF THE INVENTION

The present invention relates to a novel process for increasing the crop of fibers in plants. More specifically, it relates to a process for increasing the fiber content of plants which form a source of fibers used in industry for the production of various products, such as paper, textile fibers like ramie, jute, flax which are generally used for making clothing, bags and fabrics generally; cordage fibers which are generally used for making ropes, such as sisal, abaca and henequen; stuffing and upholstery materials, known also as "vegetable horsehair" which are obtained from coconut palms etc. The process of the invention results in an increase of the fiber content of the plants which form the source of such commercially important fibers, and thus there is obtained a substantially increased overall crop. The invention further relates to novel compositions used for application to growing plants in order to increase the fiber content of the plants.

The process of the present invention also improves the quality of the fibers; the size of same and the thickness of the cell walls is increased.

BACKGROUND OF THE INVENTION

A wide variety of plants is used as source of fibers which are used in various areas of industry. The overall quantity of fiber crops is very large and a process which increases the overall yield of fibers from a given crop is of outstanding commercial value. The process must be easily applicable and commercially attractive.

Amongst commercial crops which are of considerable commercial importance and which are used because of their fiber content there may be mentioned bast fibers of flax, hemp, jute, kenaf, ramie, agave fibers, pineapple fibers, coir or coconut fibers, kapok; and especially crops used for papermaking such as wood of various gymnospermae, esparto grass, straw, bamboo, bagasse etc.

Plant hormones are compounds which in very low concentrations cause a physiological response in plants.

It is known that auxins induce stem and root elongation. They inhibit the development of lateral buds, and they are used to propagate plants from excised stem sections called cuttings. Various auxins stimulate many kinds of cells to produce ethylene. Some auxins are known as effective herbicides. It has been hitherto the view that "Auxin is not a component of the stimulus for fiber differentiation" (Sachs, T. Ann.Bot. 36 189-197, 1972).

Gibberellins are known to promote extensive growth of plants, to induce cell elongation of various types of plant cells, including fibers. Gibberellin is known to increase the amount of fibers in plants. Gibberellin also promotes the growth of dormant buds.

Various books deal with Fibers; Vegetable Fibers, R. H. Kirby, Interscience Pub. N.Y., 1963 and Fiber Crops, Dempsey, Uni.Press of Florida, 1975. None of these provides information on compositions adapted to increase substantially fiber yields of plants used commercially for this purpose.

SUMMARY OF THE INVENTION

According to the present invention there is provided a process, and compositions for carrying out such process, which results in a pronounced increase in the quantity of vegetable fibers in plants used commercially as fiber sources for industry. The quality of the fibers is improved: fibers of increased length and of thicker cell walls are obtained. According to the present invention plants are treated with a combination of plant hormones, namely auxin and gibberellin, and this results in the desired increase of fiber content of the plants. The compositions used for this process are not expensive and the process is a very economical one as only small quantities are needed in order to result in substantially increased fiber crops.

The process of the present invention is applicable to a large variety of plants, belonging to various plant families. It is applicable to plants of the angiospermae families, of the gymnospermae etc. Experiments have shown that it is applicable to a wide variety of plants used commercially for fiber production. More extensive experiments were carried out with *Hibiscus cannabinus* L., which is known also as Kenaf and which is a source of fibers used for various purposes (such as rope and paper production, for uses similar to that of jute and the like) as well as with *Helianthus annuus* L. (Sunflower) and *Eucalyptus camaldulensis*. Auxin (NAA) by itself, and gibberellin ($GA_3$) by itself, even at comparatively high concentrations, do not give an effect which approaches that of a combination of an auxin and angibberellin in comparatively low dosages, The application of such compositions to intact plants resulted in an increase in the number of primary and secondary fibers and thus in the overall fiber content of the crop. This effect of a combination of an auxin and gibberellin is the more surprising as auxin was hitherto considered not to have any effect in this respect (see T. Sachs, above). The combination of auxin and Gibberellin results in the formation of a large number of fibers. It seems that the main effect of NAA is to increase the width of the fiber cell walls while that of $GA_3$ is an increase of the length of the fiber cells.

Auxin (referred to hereinafter as NAA) and Gibberellin (referred to as $GA_3$) can be used in various proportions, the ratio of 1:10 by weight is optimal. Ranges of about 1:5 to 1:20 still give satisfactory results. The ratio can be varied according to the desired effects. When a ratio of high NAA/low $GA_3$ is used, thick and short stems are obtained. When low NAA/high $GA_3$ is used, long and thin stems are obtained. In both cases there results a pronounced increase of fiber content of the plant.

The application of adequate concentrations of NAA and $GA_3$ at a 1:10 ratio results in a very pronounced increase of fiber numbers and thus of fiber yield. Long fibers have a high commercial value and thus the significant increase of fiber crops obtained from kenaf (*Hibiscus cannabinus* L.) is commercially significant. Various plants can be treated in a similar manner. Experiments with *Cannabis sativa* L, *Corchorus olitorius* L and *Boehmeria nivea* L Gaud show a significant increase of fiber yield. The fibers of these can be used in various industries in the production of paper, textiles, sacks etc.

The quantities of the compositions according to the invention which are needed is low and thus the cost of the process is economically attractive. The compositions were applied as spray. Large areas of crops can be sprayed at predetermined intervals of time and the resulting harvest contains appreciably increased quantities of fibers.

Various gibberellins (from $GA_1$ to $GA_{40}$), various auxins, both natural and synthetic can be used. There can also be used precursors of these which are converted in the plant into the active compounds. Many auxins are known, such as for example NAA, IBA, 2,4-D, 2,4,5-T, MCPA, IAA, indole ethanol, indoleactonitrile, etc. The various compounds are active, and the user has to choose the specific combinations and quantities according to the crop and cultivation conditions.

The following detailed description is by way of example and illustration only. It is to be understood that the process of the present invention, using compositions containing a combination of an auxin and gibberellin, results in appreciably increased fiber crops in a wide variety of plants used as fiber source.

DETAILED DESCRIPTION

*Hibiscus cannabinus* (Kenaf), *Helianthus annuus* (Sunflower) *Populus alba* and *Eucalyptus camaldulensis* plants were used in the following experiments. All the experiments were run in the summer (May-August). In each experiment ten plants were used per treatment. The plant hormones were applied to intact plant shoots. The shoots were sprayed with varying combinations of the hormones every 5 days or once a week during 12 weeks. The auxin, naphthaleneacetic acid (NAA) and the gibberellin, gibberellic acid ($GA_3$) were applied as solutions in distilled water in the concentrations (mg per liter) shown in the Table. In each application 1 mg NAA per 1 Kg fresh weight of treated plant was given when 10 mg/l NAA was applied (treatment B), whereas 10 mg $GA_3$ per 1 Kg fresh weight of plant was applied when 100 mg/l $GA_3$ was given (treatment C).

The Helianthus, Eucalyptus and Populus plants were grown in the field. The Hibiscus plants were grown in the greenhouse each in its own pot. Seedlings of 3 weeks old were selected for the experiments when Helianthus and Hibiscus were studied. Young trees of 10 months old were used when the effect of the hormones was demonstrated on Eucalyptus. The secondary xylem fiber differentiation was studied on freshly cut cross-sections taken from the middle of the plant. The sections were stained with 2% lacmoid in 96% ethanol. The walls of the fiber cells were stained blue by the lacmoid. Fiber length was measured after they were isolated by maceration in 5% KOH.

Large Fibers are obtained (on the average an increase of fiber length by about 35%), and the cell wall of the fibers is much thicker.

The following Table shows typical results of the effect of auxin (NAA) and gibberellin ($GA_3$) on the differentiation of fibers in the secondary xylem:

TABLE 1

(Quantities in mg/liter)

| Treatment | A fibers/ radius | B | C | D | E | F | G |
|---|---|---|---|---|---|---|---|
| NAA | distill water control | 10 mg/l | | 10 mg/l | 20 mg/l | | 20 mg/l |
| $GA_3$ | | | 100 mg/l | 100 mg/l | | 200 mg/l | 200 mg/l |
| *Hibiscus cannabinus* (Kenaf) | | | | | | | |
| (1) Number of fibers* | 530 ± 65 | 570 ± 62 (8%) | 705 ± 88 (33%) | 1056 ± 105 (100%) | 595 ± 82 (13%) | 814 ± 97 (54%) | 1070 ± 145 (100%) |
| (2) Total plants weight (gr) | 22 ± 3 | 21 ± 3 (−5%) | 25 ± 2 (15%) | 44 ± 3 (97%) | 19 ± 3 (−14%) | 32 ± 4 (43%) | 33 ± 3 (48%) |
| (3) Total plants height (cm) (mm) | 112 ± 4 | 110 ± 4 (−2%) | 150 ± 5 (34%) | 163 ± 4 (46%) | 110 ± 5 (−2%) | 160 ± 5 (42%) | 144 ± 4 (29%) |
| *Helianthus annuus* (sunflower) | | | | | | | |
| (1) Number of fibers* | 112 ± 13 | 121 ± 2 (8%) | 107 ± 26 (−4%) | 309 ± 53 (176%) | | | |
| (2) Total plants weight (gr) | 112 ± 18 | 106 ± 20 (−5%) | 103 ± 23 (−8%) | 257 ± 22 (131%) | | | |
| (3) Total plants height (cm) | 80 ± 5 | 80 ± 3 | 112 ± 4 (40%) | 146 ± 2 (82%) | | | |
| *Eucalyptus camaldulensis* | | | | | | | |
| (1) Number of fibers | 765 ± 32 | | | | 790 ± 26 (3%) | 860 ± 37 (12%) | 1104 ± 59 (44%) |
| (2) Total plants weight (gr) (above 75 cm height, upper part of plant) | 148 ± 54 | | | | 162 ± 24 (9%) | 186 ± 23 (26%) | 250 ± 40 (69%) |
| (3) Total plants height (cm) (above 75 cm) | 115 ± 7 | | | | 104 ± 5 (−9%) | 146 ± 6 (27%) | 149 ± 10 (30%) |

*in a cross-section, see next page

TABLE 2

*Populus alba*
Results after 10 Weeks of Spraying

| Treatment: | Untreated (Control plants) | 10 mg/l NAA + 100 mg/l $GA_3$ |
|---|---|---|
| (1) Relative area of fibers at | 204 ± 72 | 299 ± 24 |

TABLE 2-continued

*Populus alba*
Results after 10 Weeks of Spraying

| Treatment: | Untreated (Control plants) | 10 mg/l NAA + 100 mg/l GA$_3$ |
|---|---|---|
| 50 cm above ground (in cross-section) | | (+47%) |
| (2) Relative area of fibers at 100 cm above ground (cross-section) | 44 ± 17 | 209 ± 27 (+368%) |
| (3) Trunk weight (without leaves) [gr] | 47.8 ± 9 | 70.4 ± 8 (+46%) |
| (4) Total plant height [cm] | 100 ± 3 | 135 ± 7 (+35%) |

The main effect was on young plants. After 24 weeks the average height of treated plants was 225 cm while that of untreated ones under the same conditions was 130 cm.

The number of fibers in the Table was taken in Hibiscus from the middle of the plant, in Helianthus from the lower part of the stem and in Eucalyptus from the upper internodes (120 cm above the ground). In Eucalyptus the main effect of the hormones was found in the upper parts of the stem (above 75 cm).

The experiments with Hibiscus and Eucalyptus show that treatments with GA$_3$ (runs C and F) result in a limited increase of fiber content. Runs B and E show that NAA by itself has a limited effect on fiber differentiation. Best results are obtained when NAA and GA$_3$ are applied together in the ratio of 1:10 (treatments D and G). In these treatments (D and G) the fibers were also elongated and the overall crop was substantially larger than that of the control plants.

In various experiments we have found that the ratio of 1:10 of NAA with GA$_3$ gives the best results. The above Table demonstrates the general effect of the mixture of both hormones in the ratio of 1:10 to substantially increase fiber crops in various plant species by applying NAA and GA$_3$ in the form of spray.

Similar experiments with a wide variety of plants cultivated for their fiber content indicates that similar results can be attained by such treatments. The highest number of fibers were obtained in the fast growing parts of the stem. There is obtained a highly significant increase of the quantity of fibers obtained from such crops and the resulting increase is of high value, which by far exceeds the costs of the treatment by the process of the invention.

I claim:

1. A process for increasing the fiber crop of plants of the angiospermae families, selected from Hibiscus sp., Populus sp., Eucalyptus sp., Helianthus sp., Corchorus sp., and Boehmeria sp., cultivated for their fiber content, which comprises applying to said plants during the active period of the growth of the vegetative parts of the stem of the plants, a plurality of times at about weekly intervals, a composition consisting essentially of a fiber-increasing effective amount of a combination of the auxin NAA and the gibberellin GA$_3$ at a weight ratio of GA$_3$ to NAA of from 5:1 to 20:1 at a concentration in aqueous solution of from 5 to 20 mg/liter NAA and 50 to 200 mg/liter GA$_3$.

2. A process according to claim 1, wherein the quantity of NAA auxin applied to the growing plant is about 1 mg/kg fresh weight of the plant and that of the gibberellin GA$_3$ is about 10 mg/kg fresh weight of the plant.

3. A process according to claim 1, wherein the aqueous solution of the NAA and the GA$_3$ is applied to the plant by spraying until the leaves are substantially wet.

4. A process according to claim 2, wherein the aqueous solution of the NAA and the GA$_3$ is applied to the plant by spraying until the leaves are substantially wet.

* * * * *